(12) United States Patent
Bekkers et al.

(10) Patent No.: US 6,409,032 B1
(45) Date of Patent: Jun. 25, 2002

(54) ASSEMBLY OF CONTAINER AND BREAK-OFF CLOSURE AND METHOD OF PRODUCING IT

(75) Inventors: Henricus Antonius Maria Bekkers, GH Mierlo (NL); Terence Edward Weston, Stradbroke (GB)

(73) Assignees: Plastic Moulding Appliances BV, Mierlo (NL); Weston Medical Limited, Stradbroke (GB)

( * ) Notice: Subject to any disclaimer, the term of this patent is extended or adjusted under 35 U.S.C. 154(b) by 0 days.

(21) Appl. No.: 09/273,802

(22) Filed: Mar. 17, 1999

Related U.S. Application Data

(63) Continuation of application No. PCT/GB97/02499, filed on Sep. 17, 1997.

(30) Foreign Application Priority Data

Sep. 18, 1996 (NL) .............................................. 1004059

(51) Int. Cl.[7] .................................................. B65D 1/02
(52) U.S. Cl. ......................... 215/48; 215/49; 215/232; 215/250; 264/328.8
(58) Field of Search ........................... 215/48, 49, 250, 215/47, 232; 264/328.1, 328.7, 328.8

(56) References Cited

U.S. PATENT DOCUMENTS

| | | | | |
|---|---|---|---|---|
| 3,083,858 A | * | 4/1963 | Biedenstein | 215/48 X |
| 3,974,008 A | * | 8/1976 | Choksi | 215/232 X |
| 4,091,949 A | * | 5/1978 | Fowles et al. | 215/232 X |
| 4,111,324 A | * | 9/1978 | Winchell | 215/232 |
| 4,153,173 A | * | 5/1979 | Ward et al. | 215/232 |
| 4,176,755 A | * | 12/1979 | Winchell | 215/48 |
| 4,405,053 A | * | 9/1983 | Cherot | 215/48 |
| 4,448,324 A | | 5/1984 | Jeppsson et al. | |
| 4,566,613 A | | 1/1986 | Awscomb | |
| 5,158,192 A | * | 10/1992 | Lataix | 215/48 |
| 5,221,029 A | | 6/1993 | Stull | |
| 5,547,723 A | * | 8/1996 | Williams et al. | 428/35.7 |
| 5,911,340 A | * | 6/1999 | Uematsu | 215/250 X |

FOREIGN PATENT DOCUMENTS

| | | |
|---|---|---|
| EP | 0 328 504 | 8/1999 |
| WO | WO 96/24398 | 8/1996 |

\* cited by examiner

*Primary Examiner*—Stephen K. Cronin
(74) *Attorney, Agent, or Firm*—DarbY & Darby

(57) ABSTRACT

An assembly is provided comprising a container and a break-off closure made of plastic. The container comprises a surface with a passage opening, which opening is sealed by the break-off closure An attachment area is provided between the break-off closure and the surface of the container, which area is situated around and at a distance from the circumference of the passage opening. The attachment being obtained by heating the attachment surface of one of the container and break-off closure to such a temperature that a breakable attachment is formed between them.

7 Claims, 1 Drawing Sheet

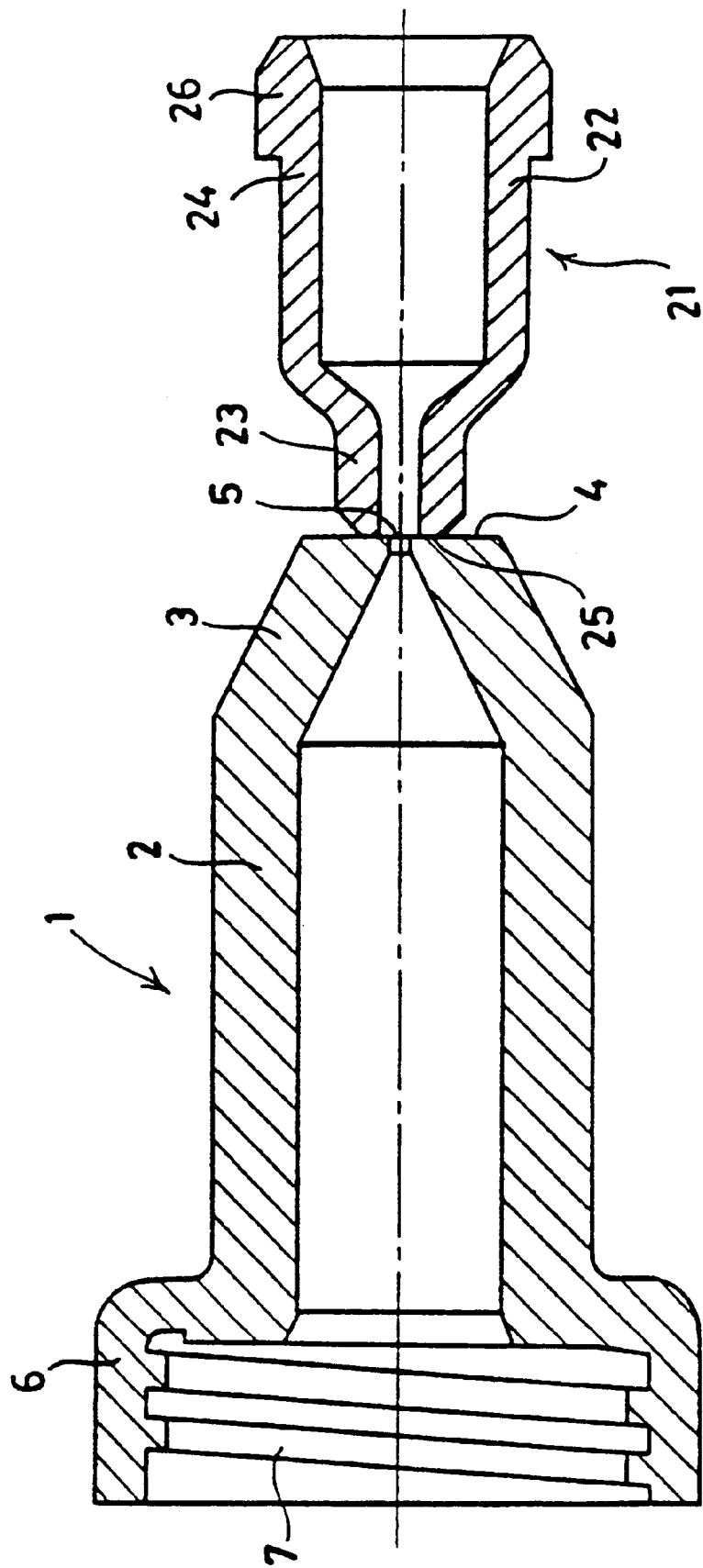

ASSEMBLY OF CONTAINER AND BREAK-OFF CLOSURE AND METHOD OF PRODUCING IT

This is a continuation of International Application No. PCT/GB97/02499, filed Sep. 17, 1997, the entire disclosure of which is hereby incorporated by reference.

The invention relates to an assembly of a container and a break-off closure made of plastic, the container comprising a surface with a passage opening, which opening is sealed by the break-off closure.

Such an assembly of a container and a plastic break-off closure is known. Assemblies of this kind are used, inter alia, in needle-free injection systems, eye-droppers nd in ampoules and the like. The break-off closure is used here to protect the contents of the container against contamination during transport and storage. Furthermore, it should be possible to remove the break-off closure easily prior to use.

From WO 96/24398 a needle-free injection system is known in which an ampoule with a discharge opening is fixed in a housing of the system by means of a nut. A break-off closure in the form of a cap is fastened to the external end of the nut, the inside of the cap being provided with a resilient seal which covers the discharge opening of the ampoule.

U.S. Pat. No. 5,221,029 discloses an integrally moulded plastic cap with break-off closure for a metering device. In the case of this known cap, an oblique groove is cut into the outer circumference of the cap, so that a less strong area is formed locally, along which area the break-off closure can be broken off.

U.S. Pat. No. 4,566,613 discloses a similar metering device with a conical end part in which two break-off zones are present.

In the devices according to the abovementioned United States patents, the break-off area is predetermined in such a way that this area is situated slightly recessed with respect to the surrounding surface of the container, so that projections, etc. formed as a result of the breaking operation do not project beyond this surface of the container and thus reduce the risk of injury when the container is placed against the body of a person or animal or against a plant or is brought close thereto.

However, a drawback of these known assemblies is that the break-off surface is not smooth but continues to include sharp points and the like, which can easily injure the person removing the break-off closure if his/her finger(s) brush over the break-off surface formed during the breaking operation. Furthermore, projections of this kind can still cause injuries to the skin of an object to be treated when the container is pressed onto the skin after the breaking operation, as is the case for needle-free injection systems.

Yet a further drawback of the metering devices according to the abovementioned United States patents is that the passage opening of the container opens into a recess which widens from the opening towards the rim. This is undesirable in needle-free injection systems, since the medium to be injected will flow from the opening along the wall of this recess and thus the injection site is no longer precisely located. Moreover, there is a risk of there being no injection whatsoever, since the pressure per surface unit is insufficient for this.

Another drawback of the break-off closure known from U.S. Pat No. 5,221,029 is that the groove has to be made by means of a subsequent machining operation, which is labour-intensive and increases the cost.

An object of the invention is therefore to provide an assembly of a container and break-off closure in which safety is improved for the user.

Another object of the invention is to provide an assembly of this kind in which the break-off area does not contain any projections after the breaking operation, so that the risk of injury is reduced both for the person removing the break-off closure and the user or consumer.

A further object of the invention is to provide an assembly of this kind for use in needle-free injection systems, in which the exact position and dimensions of the discharge opening of the container are maintained and are not interfered with by the break-off area.

The assembly of container and break-off closure of the type described above according to the invention is characterized in that the attachment area of the break-off closure to the surface of the container is situated around and at distance from the circumference of the passage opening and the attachment is obtained by heating the attachment surface of one of the container and break-off closure to such a temperature that a breakable attachment is formed between them.

It has been found that, if only the attachment surface of one of the container and break-off closure is heated, either starting from two finished components or during the production of one of the components, to a temperature at which a liquid front or front of (highly) viscous material thereof comes into contact with a surface of a solid material of the other component, an attachment is formed between the components which is sufficiently strong during handling of the assembly but which can nevertheless easily be broken, the break-off surface formed possessing an excellent smoothness. With the result that the risk of injury during the breaking operation and when placing the break-off surface of the container against, for example, a person or animal to be treated is reduced. Furthermore, the break-off area is not situated adjacent to the passage opening of the container, so that the dimensions of the opening do not change during the breaking operation but rather the original dimensions are retained.

As already indicated above, this means that the assembly of container and break-off closure cannot be formed in one step but rather the attachment, either starting from one finished component, for example the container, to the other component, for example the break-off closure, is brought about during the production of the other component, or else starting from two finished components, the attachment surface of only one component is heated to the desired temperature. Obviously, the temperature is dependent on the materials used.

Examples of suitable processes for the first possibility which may be mentioned are, inter alia, injection-moulding and extrusion, injection-moulding being referred for critical applications, such as needle-free injection systems. The break-off closure is preferably attached to a finished container by injection-moulding the break-off closure. If the container has to have an accurately defined volume, the container is preferably also produced by injection-moulding.

The nature of the attachment is not precisely known, but it is assumed that the molecules of the plastic materials of the container and the break-off closure do not extend transversely over the break-off surface, so that during breaking of the closure it is only necessary to break off a few molecules and a smooth break-off surface is obtained.

The plastic material to be used for manufacturing the break-off closure can be easily selected by the skilled person. However, in view of the intended applications of the assembly according to the invention the plastic should preferably be chosen from plastic materials, which are impermeable, strong and tough.

A material which has proven particularly suitable is polyethylene terephthalate (PET). This is unexpected, since PET is a strong plastic material. Furthermore, this material provides the advantage that it is inherently transparent, so that the contents of the container are easily visible, as is desired in the case of medicaments.

In order to increase further the breakability of the break-off closure, the strength of the break-off closure can advantageously be reduced at the position of the attachment by locally reducing the wall thickness, as is already known per se in the prior art.

According to a particularly preferred embodiment, the assembly is a cartridge for a needle-free injection system, the container comprising a substantially planar contact surface for placing against the skin of an object to be treated, with the passage opening therein, and the break-off closure is a cylindrical element, one end of which being attached to the container around and at a certain distance from the passage opening.

For use as a cartridge or ampoule for a needle-free injection system, a cylindrical element, for example a sleeve or ring, is used as the break-off closure, which element is attached to the planar front surface of the container by means of the attachment according to the invention. An element of this kind is required in order to be able to fill the container with the liquid to be metered after affixing the break-off closure. After filling the container, the other end is closed by a permanent closure element. In order to prevent the risk of the dimensions of the passage opening—which in this application has a diameter of about 0.3 mm—changing as a result of breaking the break-off closure, with all the attendant disadvantages for the injection, the attachment surface and therefore the break-off area is positioned at a distance from the opening.

It should be noted that it is already known per se from U.S. Pat. No. 4,448,324 to produce a tear-off cover for a container by means of a multi-stage injection-moulding method. However, in this case the tear line is not situated at a distance from the opening.

The invention also relates to a method of producing an assembly of a container and a break-off closure made of plastic, the container comprising a surface with a passage opening, which opening is sealed by the break-off closure which method is characterized in that the attachment surface of one of the container and break-off closure is heated to such a temperature that a breakable connection is formed around and at a distance from the circumference of the passage opening.

Preferred embodiments of the method according to the invention are defined in the dependent claims 10–13.

The invention will be explained below with reference to the attached drawing, in which the only figure is a diagrammatic, enlarged cross-section of a preferred embodiment of a container with break-off closure according to the invention, for use in needle-free injection systems.

In this figure, with a scale of 5:1, reference numeral 1 denotes a container which has been injection-moulded from PET for a medicament. The container 1 comprises a cylindrical centre section 2, which, viewed in the longitudinal direction, merges into a top section 3 of frustoconical shape, so that a planar contact surface 4 is present. A passage opening 5 is present in the centre of this surface 4. Furthermore, the container 1 is provided with a widened end 6, which is provided on the inside with screw thread 7. This end 6 can be screwed onto the drive mechanism (not shown) of a needle-free injection system. A plunger (not shown), which during injection is moved by the drive mechanism, is situated in the container 1.

A break-off closure 21 made of PET is injection-moulded onto this container 1. This break-off closure 21 comprises a body 22, formed by two cylindrical parts 23 and 24, respectively, which merge into one another and have different diameters. The end 25 of body 22 is injection-moulded onto the surface 4 of the container 1 concentrically with opening 5 but at a distance from its circumference, so that an attachment area is formed there, along which the break-off closure can be broken off. The break-off area formed by breaking off the break-off closure is therefore situated at a distance from the opening 5 and at the same level as surface 4, which is essential for the action of the injection system.

In order to facilitate the breaking operation, the wall thickness of element 23 decreases at the end 25 thereof adjacent to the container, the external diameter of part 23 in the embodiment depicted decreasing, so that its wall does not have to be deformed during the breaking operation. The other end of main body 22 comprises an external thickened portion 26, which provides a better grip for the breaking operation. The internal diameter of sleeve 24 increases gradually at this end, so that this end can easily be closed off by a permanent stopper or comparable element (not shown) after the container 1 has been filled.

It has been found that, after the break-off closure 21 has been broken off, a perfectly smooth surface 4 is present, so that the risk of injury is minimal both during the breaking operation and during the injection of the medicaments.

The invention is explained above with reference to a container with break-off closure for use in a needle-free injection system. It will be understood that the assembly of container and break-off closure according to the invention is suitable for all purposes in which the safety of the user is the main issue.

Instead of PET any permeable plastic, which has sufficient strength and toughness (i.e. plastic having a high E-modulus) could be used.

What is claimed is:

1. An assembly of a container and a break-off closure made of plastic, the container comprising a substantially planar surface with a passage extending to an opening in the surface, the opening having a circumference, the container and the break-off closure each having a respective attachment area by which they are sealingly attached to one another, wherein the attachment area of the said planar surface of the container is situated around and at a distance from the circumference of the passage opening, and wherein attachment of the attachment areas to one another is obtained by heating the attachment surface of one of the container and break-off closure to such a temperature that a breakable attachment is formed between them, wherein at least the break-off closure is made of polyethylene terephthalate (PET).

2. An assembly of a container and a break-off closure made of plastic, the container comprising a substantially planar surface with a passage extending to an opening in the surface, the opening having a circumference, the container and the break-off closure each having a respective attachment area by which they are sealingly attached to one another, wherein the attachment area of the said planar surface of the container is situated around and at a distance from the circumference of the passage opening, and wherein attachment of the attachment areas to one another is obtained by heating the attachment surface of one of the container and break-off closure to such a temperature that a breakable attachment is formed between them, wherein the wall thickness of the body decreases in the direction of the container.

3. An assembly of a container and a break-off closure made of plastic, the container comprising a surface with a passage extending to an opening in said surface, said opening being sealed by the break-off closure, wherein the attachment area of the break-off closure to the surface of the container is situated around and at a distance from the circumference of the passage opening, and wherein the attachment is obtained by heating the attachment surface of one of the container and break-off closure to such a temperature that a breakable attachment resulting in a smooth surface is formed between them, wherein at least the break-off closure is made of polyethylene terephthalate (PET).

4. An assembly of a container and a break-off closure made of plastic, the container comprising a surface with a passage extending to an opening in said surface, said opening being sealed by the break-off closure, wherein the attachment area of the break-off closure to the surface of the container is situated around and at a distance from the circumference of the passage opening, and wherein the attachment is obtained by heating the attachment surface of one of the container and break-off closure to such a temperature that a breakable attachment resulting in a smooth surface is formed between them, wherein the wall thickness of the body decreases in the direction of the container.

5. A method of producing an assembly of a container and a break-off closure made of plastic, the container comprising a substantially planar surface with a passage extending to an opening in the surface, the opening having a circumference, the container and the break-off closure each having a respective attachment area by which they are sealingly attached to one another, wherein the attachment area of one of the container and the break-off closure is heated to such a temperature that a breakable attachment is formed between the container and the break-off closure around the circumference of and at a distance from the passage opening, wherein the break-off closure is attached to the surface of the container inwardly of the outer edge thereof and around the passage opening by injection molding the break-off closure onto the container.

6. A method of producing an assembly of a container and a break-off closure made of plastic, the container comprising a substantially planar surface with a passage extending to an opening in the surface, the opening having a circumference, the container and the break-off closure each having a respective attachment area by which they are sealingly attached to one another, wherein the attachment area of one of the container and the break-off closure is heated to such a temperature that a breakable attachment is formed between the container and the break-off closure around the circumference of and at a distance from the passage opening, wherein the container is produced by injection molding.

7. A method of producing an assembly of a container and a break-off closure made of plastic, the container comprising a substantially planar surface with a passage extending to an opening in the surface, the opening having a circumference, the container and the break-off closure each having a respective attachment area by which they are sealingly attached to one another, wherein the attachment area of one of the container and the break-off closure is heated to such a temperature that a breakable attachment is formed between the container and the break-off closure around the circumference of and at a distance from the passage opening, wherein the break-off closure is made of polyethylene terephthalate (PET).

* * * * *